US008808171B2

(12) United States Patent
Lacombe et al.

(10) Patent No.: US 8,808,171 B2
(45) Date of Patent: Aug. 19, 2014

(54) ENDOSCOPY DEVICE AND METHOD FOR SIMULTANEOUS OBSERVATION OF SEVERAL ZONES OF INTEREST

(75) Inventors: Francois Lacombe, Chaville (FR); Bertrand Viellerobe, Nogent sur Marne (FR); Nicolas Boularot, Champigny sur Marne (FR); Francois Doussoux, Paris (FR); Aymeric Perchant, Fontenay sous Bios (FR)

(73) Assignee: Mauna Kea Technologies, Paris (FR)

( * ) Notice: Subject to any disclaimer, the term of this patent is extended or adjusted under 35 U.S.C. 154(b) by 911 days.

(21) Appl. No.: 12/300,247

(22) PCT Filed: May 11, 2007

(86) PCT No.: PCT/FR2007/000799
§ 371 (c)(1),
(2), (4) Date: Nov. 10, 2008

(87) PCT Pub. No.: WO2007/132085
PCT Pub. Date: Nov. 22, 2007

(65) Prior Publication Data
US 2010/0234686 A1    Sep. 16, 2010

(30) Foreign Application Priority Data

May 12, 2006    (FR) .................................. 06 04259

(51) Int. Cl.
*A61B 1/06* (2006.01)
*A61B 1/00* (2006.01)
*A61B 1/04* (2006.01)
*G02B 23/26* (2006.01)
*G02B 6/06* (2006.01)
*A61B 5/00* (2006.01)
*A61B 1/313* (2006.01)

(52) U.S. Cl.
CPC ................. *G02B 23/26* (2013.01); *A61B 1/043* (2013.01); *A61B 5/0084* (2013.01); *G02B 6/06* (2013.01); *A61B 1/00165* (2013.01); *A61B 5/0071* (2013.01); *A61B 5/0075* (2013.01); *A61B 1/313* (2013.01)

USPC ............ 600/182; 600/113; 600/109; 600/160

(58) Field of Classification Search
USPC .......... 600/129, 160, 176–178, 182; 385/117; 362/554, 574
See application file for complete search history.

(56) References Cited

U.S. PATENT DOCUMENTS 5,823,942 A    10/1998   Toida
6,826,422 B1   11/2004   Modell et al.
(Continued)

FOREIGN PATENT DOCUMENTS

EP    1 586 855      4/2004
JP    59223079 A    12/1984

OTHER PUBLICATIONS

French International Search Report corresponding to FR 06 04259.
(Continued)

*Primary Examiner* — Anhtuan T Nguyen
*Assistant Examiner* — William Chou
(74) *Attorney, Agent, or Firm* — Young & Thompson

(57) ABSTRACT

An endoscopy device includes several light guides (1, 2, 3), each light guide having one or more optical fibers. The light guides are coupled with a sweeping system (4) arranged to direct an excitation light beam in alternation in one of the fibers of the guides from the proximal end of the guide including the one of the fibers. In this way, the proximal ends of the guides may make use of the same sweeping system, whereas the distal ends of the guides may be installed simultaneously in different zones of interest of an object or animal (10) under study for an almost simultaneous observation of the zones of interest. The invention also relates to an endoscopy method used in a device according to the invention. A device and a method according to the invention may be applied to quasi-simultaneous reflectance, fluorescence, multi-photon imaging of several areas of interest.

18 Claims, 3 Drawing Sheets

(56) References Cited

U.S. PATENT DOCUMENTS

Figure 4:
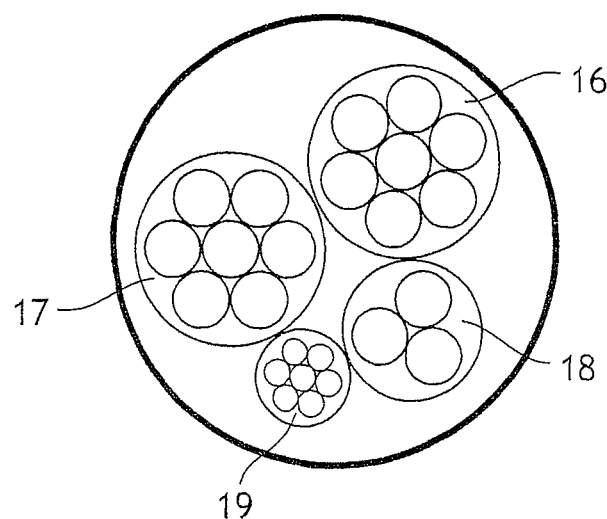

| | | | |
|---|---|---|---|
| 7,129,472 B1* | 10/2006 | Okawa et al. | 250/234 |
| 7,330,305 B2* | 2/2008 | Harris | 359/368 |
| 7,662,089 B2* | 2/2010 | Okada et al. | 600/113 |
| 8,057,083 B2* | 11/2011 | Harris | 362/574 |
| 8,475,361 B2* | 7/2013 | Barlow et al. | 600/113 |
| 2004/0037554 A1 | 2/2004 | Ferguson et al. | |
| 2004/0247268 A1* | 12/2004 | Ishihara et al. | 385/117 |
| 2005/0207668 A1 | 9/2005 | Perchant et al. | |
| 2008/0089089 A1* | 4/2008 | Hama et al. | 362/574 |

OTHER PUBLICATIONS

Flusberg et al., "Fiber-optic fluorescence imaging", Nature Methods, Dec. 2005, vol. 2, No. 12, pp. 941-950.

Gmitro et al., "Confocal microscopy through a fiber-optic imaging bundle", Optics Letters, Apr. 15, 1993, vol. 18, No. 8, pp. 565-567.

* cited by examiner

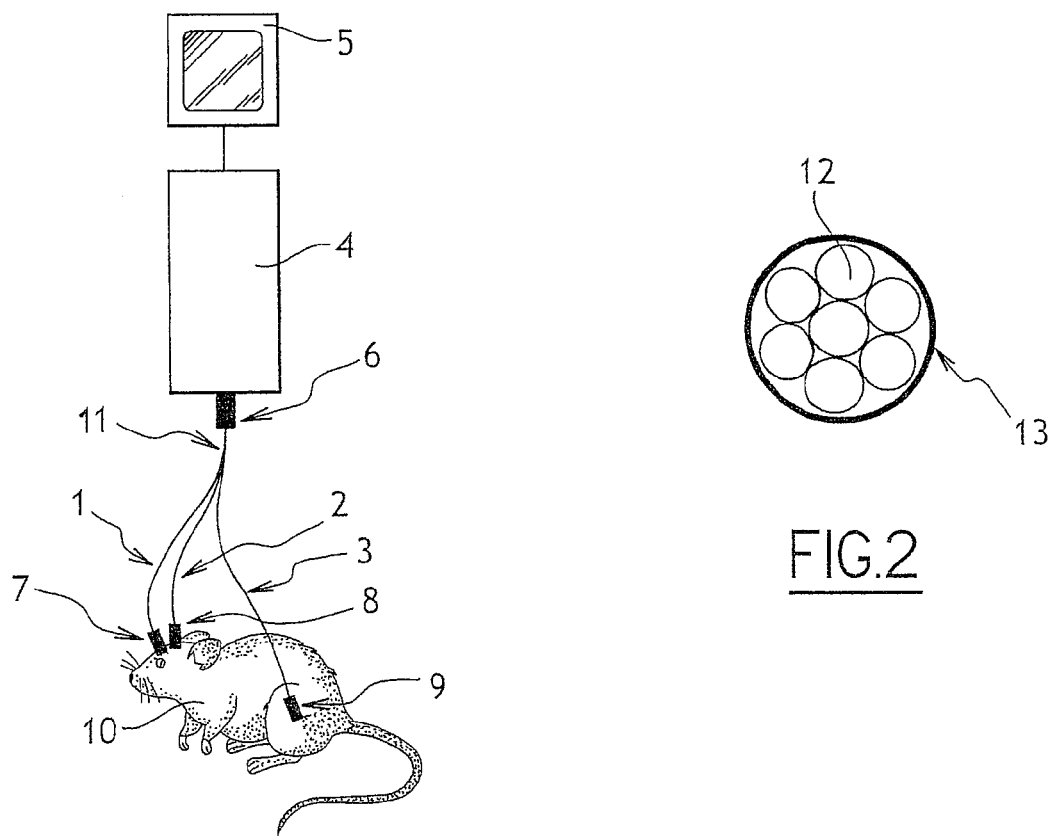
FIG.1
FIG.2
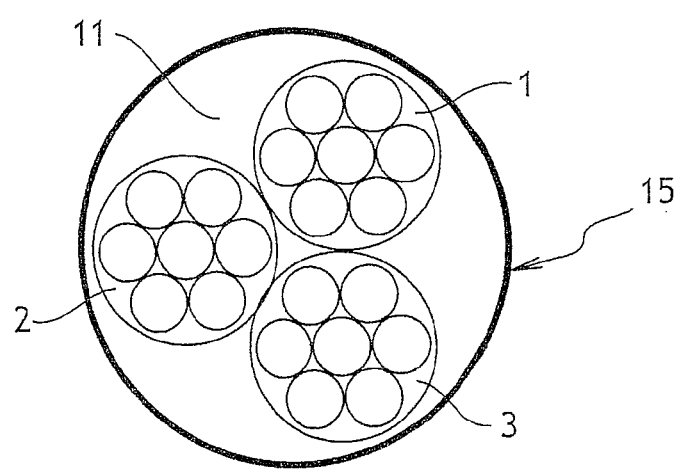
FIG.3

ENDOSCOPY DEVICE AND METHOD FOR SIMULTANEOUS OBSERVATION OF SEVERAL ZONES OF INTEREST

TECHNICAL FIELD

The present invention relates to an endoscopy device. It also relates to an endoscopy method used in a device according to the invention.

A device and a method according to the invention can be applied in a non-limitative manner to fields such as spectroscopy, in-vivo and in-situ imaging, fluorescence imaging, reflectance imaging, multiphotonic imaging, and microendoscopy.

STATE OF THE PRIOR ART

Generally, an endoscopy device comprises a light guide comprising a single optical fibre or a bundle of a plurality of optical fibres. A first end of the guide, which will hereinafter be called "distal end", is provided to be inserted into a body under examination or laid flat against the body, so as to be able to examine said body. Hereinafter the other end of the guide will be called "proximal end". The guide allows a certain flexibility of insertion, and allows a light beam to be conveyed from the proximal end as far as the distal end of the guide or vice versa.

The endoscopy device can also comprise an optical head connected to the distal end of the guide. The optical head allows an excitation light beam originating from the guide to be focused on the surface or at depth inside the body under examination. The optical head also allows a light beam to be collected and this beam to be transmitted to the guide. The guide and the optical head thus constitute a miniature confocal microscope. In order to be able to observe all of a field of view, the focused excitation beam can be scanned in the field by scanning means situated at the distal or proximal side of the guide.

When the scanning means are situated on the proximal side, the role of the light guide is to convey an image point-by-point. It must thus be constituted by a plurality of optical fibres. The term then used is an image guide.

An in-situ and in-vivo microscope examination carried out with such a device allows observation of an area of interest over only a very reduced field of view, typically approximately a few hundred micrometers across. This limitation can constitute a problem for the interpretation of phenomena manifesting themselves over a region larger than the observed field, or being interpretable only if the observed field is larger than the region in which the phenomenon occurs. This limitation is also a problem when the studied phenomenon occurs in areas of interest that are a greater or lesser distance apart from one another, in particular at great distances beyond any reasonably observable field.

To provide the possibility of observing several areas of interest with a sufficient resolution would allow this limitation to be resolved. For example, in the case of imaging of the nervous system in small animals, different regions of the brain or different nerve-endings, or both, could be observed on a microscopic scale. Another example consists of the study of vascular phenomena, where a blood network could be the subject of a multiple observation of several sites.

The purpose of the present invention is to propose an endoscopy device providing the possibility of simultaneously or virtually-simultaneously observing several areas of interest.

DISCLOSURE OF THE INVENTION

This objective is achieved with an endoscopy device comprising several light guides each comprising two ends, respectively proximal and distal, linked by one or more optical fibres, and a scanning system optically linked to said proximal ends and arranged to direct an excitation light beam into one of the fibres of said light guides in turn.

Preferably, the light guides comprise a plurality of optical fibres. The term then more likely to be used is image guides.

Thus, the same scanning system can direct an excitation light beam into more than one light guide, so that several light guides make use of the same scanning system. The illumination of the proximal ends of the fibres one by one is transmitted by these to their distal ends, where each fibre in turn becomes a source of illumination. Each light guide is a probe, the independent distal end of which can be installed simultaneously with other probes in or on a different area of interest of a studied object, system or animal. The device according to the invention therefore allows, for example, the production of in-vivo, in-situ and simultaneous imaging of several distinct areas of interest of a single animal. The dimensions of the light guides can be small enough (typically a few hundred micrometers in diameter) for each light guide to constitute a microendoscopic probe which requires very little space. The number of fibres and the dimension of the fibres can vary from one guide to the other.

The scanning system can consist of any system ordinarily used to scan an input surface of an image guide. The scanning system can for example comprise two different mirrors, ensuring the horizontal and vertical scanning of the input surface of the light guides.

The proximal ends of the light guides can be combined to form a bundle of light guides, the bundle of light guides thus having a proximal end grouping together the proximal ends of the light guides. The device according to the invention can then also comprise means for connecting the proximal end of the bundle of guides to the scanning system. In an embodiment of a device according to the invention, the light guides can be arranged to retain, at the proximal end of the bundle of guides, an arrangement of the fibres from one guide to the other, in particular when the scanning system operates only with fibres arranged at the proximal end of the bundle of guides. In another embodiment of a device according to the invention, the fibres from one guide to the other at the proximal end of the bundle of guides can be arranged in any way whatever, in particular when the scanning system is adapted to fibres randomly distributed at the proximal end of the bundle of guides.

The device according to the invention can also comprise a light source for emitting the excitation light beam.

The device according to the invention can also comprise an optical head arranged on a distal end of one of the light guides. The optical head can in particular allow the focusing in a focal plane of the excitation light beam transmitted to the optical head by a fibre of said one of the guides, and can also allow a light beam reflected or emitted substantially in this focal plane to be collected and the collected beam to be transmitted to the same fibre. Depending on the optical head used, the excitation beam can be focused on the surface or at depth.

The device according to the invention can also comprise means of detecting a light beam collected at the distal end of one of the light guides. These detection means can for example comprise a spectrometer, a photomultiplier or a photodiode which detects a light beam collected by a fibre in response to the excitation beam directed into this same fibre, or also a sensor comprising a plurality of pixels such as a CCD sensor, the pixels of which detect in turn the light beam collected in response to the excitation beam. The detection means are therefore preferably arranged to detect a light beam collected at the distal end of a fibre of one of the guides in response to the excitation beam directed into this same fibre, this fibre therefore carrying out a spatial filtering of the light collected at the distal end of the guide, which makes the device according to the invention confocal.

The device according to the invention can also comprise means for extracting, from the beams collected by one or more guides, a set of light beams collected by several fibres at the distal end of one of the light guides, and can also comprise means for constructing an image from the set of collected light beams. Preferably, the beams of the set are collected in turn by the fibres and during a scanning period if the scanning is periodic. Typically, these extraction means comprise means for implementing an extraction algorithm
using a correspondence table between each fibre and pixels of a detector, or a correspondence table between each fibre and a moment of the scanning period if the scanning is periodic, such that the extraction means can associate each beam detected by the detector with the fibre from which the beam originates. The extraction means can allow the collected light beams to be grouped together according to the light guide collecting the beams. For each light guide, the constructed image then corresponds to a field of view of a area of interest. The size of the field of view and the observation depth depend on the number and the diameter of the fibres in the guide, and optionally on the characteristics of the optical head arranged at the distal end of the guide. The device according to the invention can also comprise means for displaying the image.

Generally, a device according to the invention can also comprise means for acquiring and processing an image and which implement a method as described in patent application WO 2004/010377 A1.

The device according to the invention can also comprise means for varying the spectral content of the excitation light beam depending on the light guide into which the excitation light beam is directed. Preferably, a different wavelength can be associated with each light guide. The combined means of varying the spectral content and the scanning system constitute polychromatic scanning means, which can allow simultaneous excitation of the different stains present in the different areas of interest.

According to yet another aspect of the invention, an endoscopy method implemented in a device according to the invention is proposed, comprising:
  a coupling of several light guides to a scanning system, each light guide comprising two ends, respectively proximal and distal, linked by one or more optical fibres, and
  a scanning of the guides by the scanning system, the scanning directing an excitation light beam in turn into one of the fibres of the guides from the proximal end of the guide comprising said one of the fibres.

The method according to the invention can also comprise a collection of a light beam at the distal end of one of the light guides. The method according to the invention can also comprise detecting the collected light beam. The collected light beam may come from a reflection or from a re-emission of the excitation beam, and therefore there is generally a detection in turn of a collected light beam at the distal end of the fibre into which the excitation beam is directed in turn. The method according to the invention can therefore comprise detecting a light beam collected at the distal end of a fibre of one of the guides in response to the excitation beam directed into this same fibre, this fibre therefore carrying out a spatial filtering of the light collected at the distal end of the guide.

The method according to the invention can also comprise a creation or generation of a correspondence table between each fibre and pixels of a detector which detect a beam collected at the distal end of the fibre. Similarly, if the scanning is periodic, the method according to the invention can also comprise a creation or generation of a correspondence table between each fibre and a moment, in the course of the scanning period, during which a beam collected at the distal end of the fibre is detected.

The method according to the invention can also comprise a variation of the spectral content of the excitation light beam depending on the light guide into which the excitation light beam is directed.

The scanning can be periodic. In the course of a scanning period, the scanning can for example either direct the excitation light beam along a frame common to several light guides, or direct the excitation light beam along several successive frames, each of the successive frames scanning a given light guide.

The scanning can direct the excitation light beam along parallel lines.

The scanning can direct the excitation light beam only into certain fibres of certain of the light guides.

The method according to the invention can also comprise an extraction of a set of light beams collected by several fibres at the distal end of one of the guides, can also comprise a construction of an image from the set of collected light beams, and can also comprise a display of the image. The beams of the set can be collected in turn by the fibres and during a scanning period if the scanning is periodic. Extraction can be achieved using the correspondence table between each fibre and pixels of a detector or using the correspondence table between each fibre and a moment in time during a scanning period. Thanks to these tables, it is not necessary to preserve the arrangement of the fibres from one guide to the next in order to construct images, which represents a real advantage inasmuch as it greatly reduces the constraints concerning the coupling of the guide to the scanning system, and the constraints concerning the arranging of the fibres from one guide to the next, for example when they are assembled in a bundle of guides.

In the device and the method according to the invention, the excitation light beam can be monochromatic or polychromatic, and can be continuous or pulsed. The device and method according to the invention can be applied to fluorescence, reflectance, or also multiphotonic imaging.

DESCRIPTION OF FIGURES AND EMBODIMENTS

Figure 5:
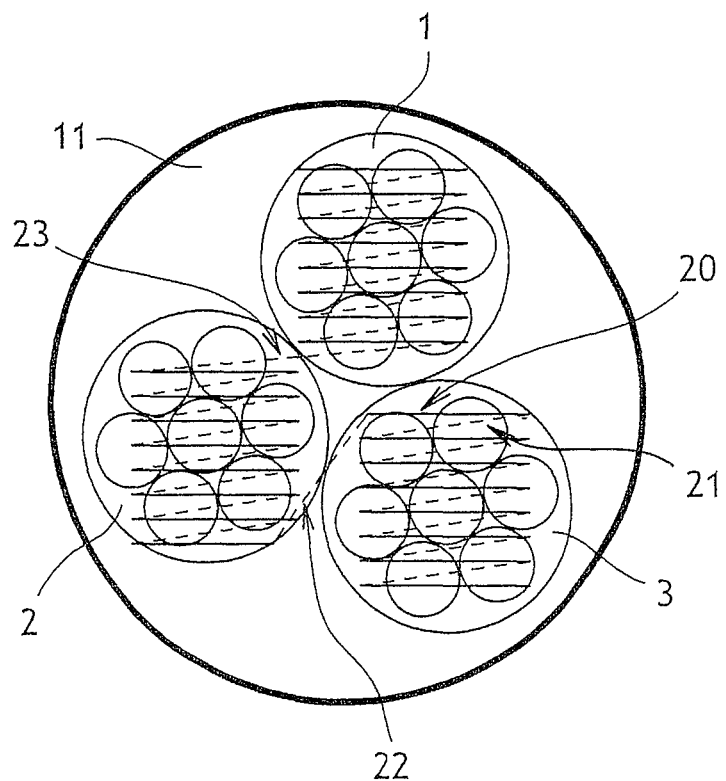
Figure 6:
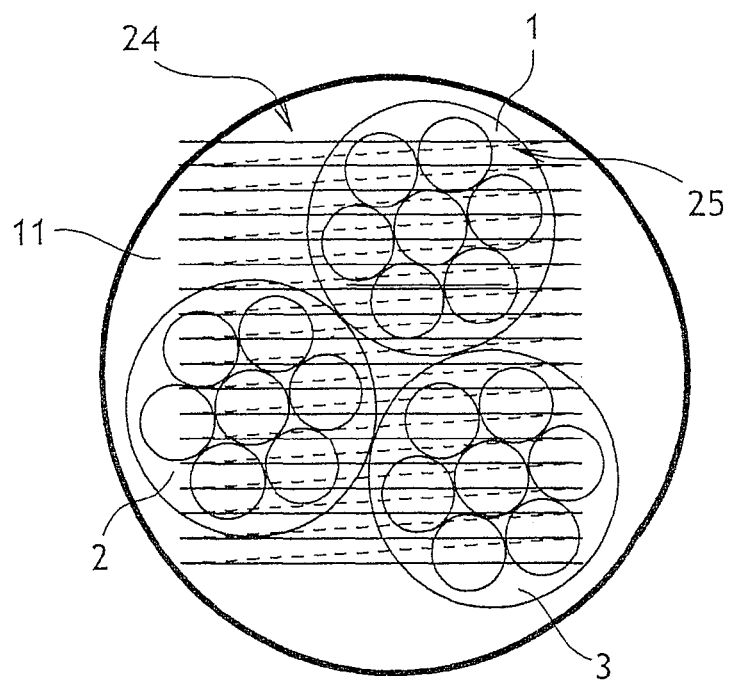
Figure 7:
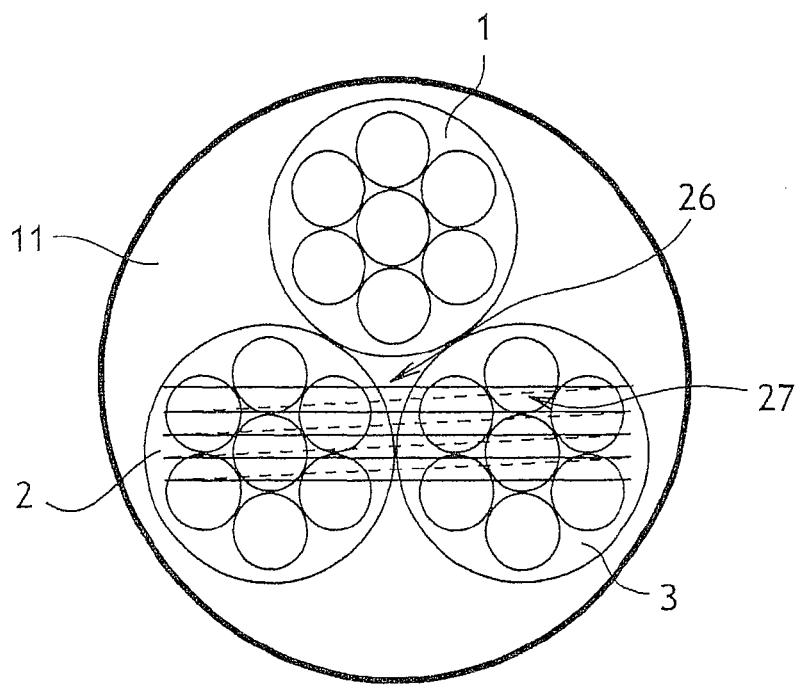

Other advantages and characteristics of the invention will become apparent on examination of the detailed description of embodiments which are in no way limitative, and the following attached drawings:

FIG. 1 illustrates a first embodiment of a device according to the invention,

FIG. 2 illustrates a cross-section view of one of the image guides of the first embodiment of a device according to the invention, FIG. 3 illustrates a cross-section view of a bundle of image guides of the first embodiment of a device according to the invention, FIG. 4 illustrates a cross-section view of a bundle of image guides of a second embodiment of a device according to the invention, FIG. 5 illustrates a scanning of a first embodiment of the method according to the invention, FIG. 6 illustrates a scanning of a second embodiment of the method according to the invention, and FIG. 7 illustrates a scanning of a third embodiment of the method according to the invention.

There will first be described, with reference to FIGS. 1, 2 and 3, a first embodiment of a device according to the invention, which is a preferred embodiment of a device according to the invention.

The first embodiment of a device according to the invention illustrated in FIG. 1 comprises three image guides 1, 2, 3, a housing 4 comprising a scanning system, and a display screen 5.

FIG. 2 illustrates a cross-section view of the distal end of one of the image guides. Each image guide is more or less identical and consists of a bundle of optical fibres, comprising several thousand optical fibres cores 12, not regularly arranged. The arrangement of the fibres of a guide 1, 2 or 3 is not preserved from one guide to another guide at the proximal end of the bundle 11 of the guides. At their distal end, each image guide is also surrounded by a protective sheath 13. The diameter of the fibres is several micrometers, and the diameter of the guides is several hundred micrometers. For greater clarity, a limited number of fibres has been shown in FIG. 2, and similarly a limited number of fibres per guide will be shown in the following figures. The distal end of each image guide is independent of and separated from the distal ends of the other image guides. Each distal end of a guide can therefore move independently of the other image guides, and the distal ends of the image guides can therefore be installed simultaneously in different areas of interest of an animal 10.

The proximal ends of the image guides are combined to form a bundle 11 of image guides. FIG. 3 illustrates a cross-section view of the bundle 11 of image guides. In order to produce the bundle 11 of guides, the proximal ends of the three image guides 1, 2, 3 have been separated from their protective sheath 13 then bonded together. The whole is surrounded by a protective sheath 15. The proximal end of the bundle 11 of guides groups together the proximal ends of the guides, which thus form a scanning-input surface for an excitation light beam. The bundle 11 of guides is connected via a connector 6 to the housing 4 so as to present the proximal end of the bundle 11 of guides to the scanning system.

The scanning system comprises two different mirrors which direct an excitation light beam in turn into one of the fibres of the guides from the proximal end of the bundle 11 of the guides, this illumination of the fibres one by one being transmitted by these as far as their distal end where each becomes in turn a source of illumination.

The distal end of each image guide 1, 2, or 3 is connected to an optical head 7, 8, or 9, which:
  focuses the excitation light beam, originating from a fibre, onto the surface or at depth in the area of interest of the animal 10 in which the optical head is installed,
  collects a light beam reflected or re-emitted by the biological tissue illuminated in this area of interest, and
  transmits the collected beam to the same fibre.

The collected light beam is then transmitted from the distal end as far as the proximal end of the image guide, and is directed towards the interior of the housing 4 as far as a light beam detector.

The scanning of the proximal end of the bundle 11 of guides is periodic, and the housing 4 also comprises means for extracting, from all the light beams detected by the detector during a period, a set of light beams collected at the distal end of one of the guides by several fibres of said guide. The housing 4 also comprises an image-synthesis module which constructs an image from the set of beams. The display screen 5 displays this image. The display screen can thus display an image for each of the image guides 1, 2, or 3.

The housing 4 also comprises a laser emitting the excitation light beam in continuous or pulsed mode, and means of varying the spectral content of the excitation light beam. The variation means can be programmed to direct an excitation light beam of a given wavelength per image guide.

Numerous possible variants exist based on the first embodiment of a device according to the invention, in particular as regards the number of guides, the number of fibres per guide, the diameter of the fibres and the diameter of the guides. For example, the variant for which the proximal ends of seven guides are combined in a bundle of guides applies equally well to the case of guides of the same diameter.

A second embodiment of a device according to the invention comprises all the same elements as the first embodiment of a device according to the invention, except that it comprises not three, but four, image guides the proximal ends of which are grouped together in a bundle of guides. FIG. 4 illustrates a cross-section view of a bundle of guides of the second embodiment of a device according to the invention. Two first guides 16, 17 have the same number of fibres and have fibres of the same diameter, but are not arranged to preserve, at the proximal end of the bundle of guides, an arrangement of the fibres from one guide to the other. The two other guides 18, 19 have numbers of fibres or diameters of fibres which differ from the two first guides 16, 17 and therefore each has a different diameter from the two first guides.

There will now be described, with reference to FIGS. 5, 6, and 7, first, second and third embodiments of the method according to the invention implemented in the first embodiment of a device according to the invention.

The first, second and third embodiments of the method according to the invention comprise:
  a coupling of the three image guides 1, 2, 3 to a scanning system, and
  a periodic scanning of the guides by the scanning system, the scanning directing an excitation light beam in turn into one of the fibres of the guides from
  the proximal end of the guide comprising said one of the fibres.

The first, second and third embodiments of the method according to the invention also comprise, for each fibre into which the excitation light beam is directed in turn:
  a transmission of the excitation light beam along the fibre from the proximal end as far as the distal end of the guide comprising the fibre,
  a focusing of the excitation beam by the optical head connected to the guide,
  a collection by the optical head of a light beam reflected or re-emitted by diffusion or by fluorescence,
  a transmission of the light beam collected at the distal end of the guide,
  a transmission of the excitation light beam along the fibre from the distal end as far as the proximal end of the guide, and
  a detection of the collected light beam by the detector, the fibre being connected in a correspondence table with the pixels of the detector which detect the collected beam and with the moment in time, in the course of the scanning period, during which the beam is detected.

Consequently, an excitation light beam is directed in turn into one of the fibres of the guides from the proximal end of the guide comprising said one of the fibres, and light beams collected at the distal end of this fibre are detected in turn, this fibre therefore carrying out a spatial filtering of the light collected at the distal end of the guide. Thus, the detector of the first embodiment of a device according to the invention is arranged to detect a light beam collected at the distal end of a fibre of one of the guides in response to the excitation beam directed into this same fibre, this fibre therefore carrying out a spatial filtering of the light collected at the distal end of the guide, which makes the first embodiment of a device according to the invention confocal.

The correspondence table is created during a step of calibration of the device according to the invention, after having coupled the bundle of guides to the scanning system. The first, second and third embodiments of the method according to the invention also comprise for each image guide during a period of time:
- an extraction, from all the beams detected by the detector and using the correspondence table, of a set of light beams collected by several fibres at the distal end of the guide and detected by the detector,
- a construction of an image from the set of collected and detected light beams, the image representing a field of view of an area of interest in which the optical head of the guide is installed, the construction comprising processing sufficient to eliminate the imprint of the network of thousands of fibres of the guide, and
- a display of the image on the display screen.

For the image guides 1, 2, 3 comprising several thousand fibres several micrometers in diameter, the typical surface area of the field of view is in the square millimeter range, this surface area depending in particular on the characteristics of the optical head arranged on the distal end of the guide 1, 2, or 3. By installing the optical heads in several areas of interest of an animal, the method according to the invention therefore allows an in-vivo, in-situ and simultaneous display of several areas of interests of the animal with a microscopic resolution.

FIG. 5 illustrates, on a cross-section view of the proximal end of the bundle 11 of guides of the first embodiment of a device according to the invention, a scanning period in the case of the first embodiment of the method according to the invention. In a scanning period of the first embodiment of the method according to the invention, the scanning system directs the excitation light beam in turn into a fibre from the proximal end of the bundle 11 of guides, along parallel horizontal lines 20 linked by oblique lines 21. A set of horizontal lines 20 linked by oblique lines 21 constitute a frame resembling the raster of a television screen. The horizontal lines 20 and the oblique lines 21 are arranged to form one frame per image guide 1, 2, or 3. The horizontal lines 20 do not direct the excitation beam into the gaps comprised between the proximal ends of the image guides. The frame of the first scanned guide 1 is linked to the frame of the second scanned guide 2 by a first oblique relay line 23, and the frame of the second scanned guide 2 is linked to the frame of the third scanned guide 3 by a second oblique relay line 22. Over the course of a period of time, all the fibres are scanned. The horizontal lines 20 are close enough to direct the excitation light beam more than once per period into a single fibre, which allows a high sampling resolution of the fibres. The actual technical scanning means allow the proximal end of the bundle 11 of guides to be scanned at this resolution over a period of time of a hundred or so milliseconds. The scanning time of a frame of a guide is therefore some thirty milliseconds. Three images constructed during a period, from three sets of collected beams each originating from a given guide, therefore correspond to a virtually simultaneous observation of three areas of interest in which the three optical heads are installed. The first embodiment of the method according to the invention also comprises a variation of the wavelength of the excitation light beam, such that the excitation light beam is monochromatic and of a given wavelength per guide. Thus, each image guide can serve to excite a different stain per area of interest.

FIG. 6 illustrates, on a cross-section view of the proximal end of the bundle 11 of guides of the first embodiment of a device according to the invention, a scanning period in the case of the second embodiment of the method according to the invention. In a scanning period of the second embodiment of the method according to the invention, the scanning system directs the excitation light beam in turn into one of the fibres from the proximal end of the bundle 11 of guides, along parallel horizontal lines 24 linked by oblique lines 25. The horizontal lines 24 are close enough to direct the excitation light beams more than once per period into the same fibre. During a period, all the fibres are scanned, and the horizontal lines also direct the excitation beams into the gaps comprised between the proximal ends of the image guides. The horizontal lines 24 linked by oblique lines 25 constitute a frame common to the three guides 1, 2, 3 which resembles the raster of a television screen, such that one horizontal line scans generally more than one image guide. The three image guides are therefore scanned almost simultaneously during a period, and three images constructed in the course of a period from three sets of collected beams each originating from a given guide, correspond to a virtually simultaneous observation of three areas of interest into which the three optical heads are installed.

FIG. 7 illustrates, on a cross-section view of the proximal end of the bundle 11 of guides of the first embodiment of a device according to the invention, a scanning period in the case of the third embodiment of the method according to the invention. In a scanning period of the third embodiment of the method according to the invention, the scanning system directs the excitation light beam in turn into one of the fibres from the proximal end of the bundle 11 of guides, along parallel horizontal lines 26 linked by oblique lines 27. The horizontal lines 26 are close enough to direct the excitation light beams more than once per period into the same fibre, but there are not enough of them to direct the excitation light beams into the three guides and into all the fibres of the two scanned guides 2, 3. The horizontal lines 26 linked by oblique lines 27 constitute a frame common to two of the guides 2 and 3, such that one horizontal line 26 generally scans the two guides 2, 3 scanned by the raster. The two scanned image guides 2, 3 are therefore scanned virtually simultaneously over a period of time. Scanning only certain fibres of certain guides during of a period allows the scanning period to be reduced to several milliseconds.

Of course, the invention is not limited to the examples which have just been described, and numerous adjustments can be made to these examples without exceeding the scope of the invention. In a device according to the invention, the number of image guides used, the diameter of the fibres of the guides, and the number of fibres per guide can have numerous possible values. A device according to the invention can be applied to numerous fields such as spectroscopy, fluorescence, reflectance, or multiphotonic imaging. Within the framework of multiphotonic imaging, a device according to the invention can also comprise pre-compensation means to compensate for possible dispersive effects of the fibres. These pre-compensation means can be placed at the proximal ends of the image guides, on condition that the guides have similar dispersion properties. Additionally, the proximal ends of the image guides are not necessarily coupled to the scanning system in the form of a bundle of guides, but can be separately coupled to the scanning system.

The invention claimed is:
1. Endoscopy device comprising:
   several light guides (1, 2, 3), each light guide comprising two ends, respectively a proximal end and a distal end, linked by a plurality of optical fibres (12), the distal end of each light guide being separated from the distal ends of the other light guides so that the distal end of each light guide is arranged for being moved independently of the other light guides, a scanning system optically linked to the proximal ends of all the light guides and arranged to direct an excitation light beam in turn into one of the fibres of said light guides from the proximal end of the light guide comprising said one of the fibres, and a detector arranged for, in response to the excitation beam directed by the scanning system into one fibre, detecting a light beam collected at the distal end of the same one fibre, the proximal ends of the light guides being combined to form a bundle of light guides, the light guides being arranged in such a way that, at the proximal end of the bundle of the guides, an arrangement of the fibers varies from one guide to the other in rotational alignment, translation, spacing, or diameter of the fibers, the device comprising means for extracting, from the beams collected by one or more light guides, a set of light beams collected by several fibres at the distal end of one of the light guides, these extraction means comprising means for implementing an extraction algorithm using a correspondence table between each fibre and pixels of a detector, and/or a correspondence table between each fibre and a moment of the scanning period if the scanning is periodic, such that the extraction means can associate each beam detected by the detector with the fibre from which the beam originates.

2. Device according to claim 1, characterized in that it also comprises a connector (6) for connecting the proximal end of the bundle (11) of guides to the scanning system (4).

3. Device according to claim 1, characterized in that it also comprises a light source for emitting the excitation light beam.

4. Device according to claim 1, characterized in that it also comprises an optical head (7, 8, 9) arranged on a distal end of one of the light guides (1, 2, 3).

5. Device according to claim 1, configured for varying the spectral content of the excitation light beam depending on the light guide (1, 2, 3) into which the excitation light beam is directed.

6. Device according to claim 1, configured for extracting a set of light beams collected by several fibres at the distal end of one of the light guides (1, 2, 3).

7. Device according to claim 6, characterized in that it also comprises an image synthesis module for constructing an image from the set of collected light beams.

8. Device according to claim 7, characterized in that it also comprises a display (5) for displaying the image.

9. Endoscopy method implemented in a device according to claim 1, comprising a coupling of several light guides (1, 2, 3) to a scanning system (4), each light guide comprising two ends, respectively a proximal end and a distal end, linked by a plurality of optical fibres (12), the distal end of each light guide being separated from the distal ends of the other light guides so that the distal end of each light guide is arranged for being moved independently of the other light guides, a scanning of the light guides by the scanning system, the scanning directing an excitation light beam in turn into one of the fibres of the light guides from the proximal end of the light guide comprising said one of the fibres, and in response to the excitation beam directed by the scanning system into one fibre, a detection of a light beam collected at the distal end of the same one fibre, the proximal ends of the light guides being combined to form a bundle of light guides, the light guides being arranged in such a way that, at the proximal end of the bundle of the guides, an arrangement of the fibers varies from one guide to the other in rotational alignment, translation, spacing, or diameter of the fibers, and wherein:

the process includes a creation of a correspondence table between each fibre and pixels of a detector which detect a beam collected at the distal end of the fibre, and/or the scanning is periodic, and the process includes a creation of a correspondence table between each fibre and a moment in time, during a scanning period, during which a beam collected at the distal end of the fibre is detected.

10. Method according to claim 9, characterized in that it also comprises a variation of the spectral content of the excitation light beam depending on the light guide (1, 2, 3) into which the excitation light beam is directed.

11. Method according to claim 9, characterized in that the scanning is periodic.

12. Method according to claim 11, characterized in that during a scanning period, the scanning directs the excitation light beam along a frame common to several light guides.

13. Method according to claim 11, characterized in that during a scanning period, the scanning directs the excitation light beam along several successive frames, each of the frames scanning a given light guide.

14. Method according to claim 9, characterized in that the scanning directs the excitation light beam along parallel lines (20, 24, 26).

15. Method according to claim 9, characterized in that the scanning directs the excitation light beam only into certain fibres of certain light guides (1, 2, 3).

16. Method according to claim 9, characterized in that it also comprises an extraction of a set of light beams collected by several fibres at the distal end of one of the light guides (1, 2, 3).

17. Method according to claim 16, characterized in that it also comprises a construction of an image from the set of collected light beams.

18. Method according to claim 17, characterized in that it also comprises a display of the image.

* * * * *